United States Patent
Wu et al.

(10) Patent No.: US 9,590,244 B2
(45) Date of Patent: Mar. 7, 2017

(54) NI—MN COMPOSITE OXALATE POWDER, LITHIUM TRANSITION METAL COMPOSITE OXIDE POWDER AND LITHIUM ION SECONDARY BATTERY

(71) Applicants: INDUSTRIAL TECHNOLOGY RESEARCH INSTITUTE, Hsinchu (TW); NATIONAL TAIWAN UNIVERSITY, Taipei (TW)

(72) Inventors: Hung-Chun Wu, Jhubei (TW); Yu-Ting Chen, Chiayi (TW); Nae-Lih Wu, Taipei (TW); Wen-Chin Chen, Kaohsiung (TW); Shih-Chieh Liao, Jungli (TW); Yih-Chyng Wu, Taipei (TW)

(73) Assignees: Industrial Technology Research Institute, Hsinchu (TW); National Taiwan University, Taipei (TW)

( * ) Notice: Subject to any disclaimer, the term of this patent is extended or adjusted under 35 U.S.C. 154(b) by 424 days.

(21) Appl. No.: 14/141,176

(22) Filed: Dec. 26, 2013

(65) Prior Publication Data
US 2015/0104706 A1     Apr. 16, 2015

(30) Foreign Application Priority Data

Oct. 15, 2013  (TW) .............. 102137075 A

(51) Int. Cl.
*H01M 4/00*      (2006.01)
*H01M 4/505*    (2010.01)
(Continued)

(52) U.S. Cl.
CPC ............ *H01M 4/505* (2013.01); *C01G 53/50* (2013.01); *C07C 55/07* (2013.01); *H01M 4/525* (2013.01);
(Continued)

(58) Field of Classification Search
CPC ...... C01G 53/50; H01M 4/525; H01M 4/505; H01M 4/366; H01M 10/0525;
(Continued)

(56) References Cited

U.S. PATENT DOCUMENTS 7,803,199 B2   9/2010  Kawakami et al.
7,824,807 B2   11/2010  Yuasa et al.
(Continued)

FOREIGN PATENT DOCUMENTS

CN  100362681 C   1/2008
CN  101542788 A   9/2009
(Continued)

OTHER PUBLICATIONS

Park et al., "Lithium-manganese-nickel-oxide electrodes with integrated layered-spinel structures for lithium batteries", Electrochemistry Communications, vol. 9, 2007 (published online: Oct. 19, 2006), pp. 262-268.
(Continued)

*Primary Examiner* — Gary Harris
(74) *Attorney, Agent, or Firm* — Birch, Stewart, Kolasch & Birch, LLP

(57) ABSTRACT

The disclosure provides a Ni—Mn composite oxalate powder, including a plurality of biwedge octahedron particles represented by the general formula: $Ni_qMn_xCo_yM_zC_2O_4 \cdot nH_2O$, wherein $q+x+y+z=1$, $0<q$, $x<1$, $0 \le y<1$, $0 \le z<0.15$, $0 \le n \le 5$, and M is at least one of Mg, Sr, Ba, Cd, Zn, Al, Ga, B, Zr, Ti, Ca, Ce, Y, Nb, Cr, Fe and V. The above powder may be further calcined with a lithium salt to form a lithium transition metal oxide powder for use as a positive electrode material in lithium ion-batteries.

13 Claims, 13 Drawing Sheets

(51) Int. Cl.
*H01M 4/525* (2010.01)
*C01G 53/00* (2006.01)
*C07C 55/07* (2006.01)
*H01M 10/0525* (2010.01)
*H01M 4/02* (2006.01)
*H01M 4/36* (2006.01)
*H01M 4/62* (2006.01)

(52) U.S. Cl.
CPC ...... *C01P 2002/50* (2013.01); *C01P 2002/54* (2013.01); *C01P 2004/61* (2013.01); *C01P 2004/62* (2013.01); *C01P 2004/80* (2013.01); *C01P 2004/84* (2013.01); *H01M 4/366* (2013.01); *H01M 4/62* (2013.01); *H01M 10/0525* (2013.01); *H01M 2004/028* (2013.01)

(58) Field of Classification Search
CPC .. H01M 2004/028; H01M 4/62; H01M 4/485; C07C 55/07; Y02E 60/122; C01P 2002/50; C01P 2002/54; C01P 2004/61; C01P 2004/62; C01P 2004/80; C01P 2004/84
USPC .... 429/220, 221, 222, 223, 224, 231, 231.2, 429/231.3
See application file for complete search history.

(56) References Cited

U.S. PATENT DOCUMENTS

| 2006/0099508 | A1 | 5/2006 | Thackeray et al. | |
| 2009/0224212 | A1* | 9/2009 | Manthiram | H01M 4/505 252/503 |
| 2010/0086851 | A1 | 4/2010 | Wang et al. | |
| 2011/0223493 | A1* | 9/2011 | Christian | H01M 4/06 429/344 |
| 2012/0164511 | A1 | 6/2012 | Wu et al. | |
| 2015/0333325 | A1* | 11/2015 | Sun | H01M 4/364 429/221 |

FOREIGN PATENT DOCUMENTS

| CN | 102509790 A | 6/2012 |
| CN | 102544475 A | 7/2012 |
| CN | 102569807 A | 7/2012 |
| CN | 102627332 A | 8/2012 |
| CN | 102938458 A | 2/2013 |
| JP | 2001-155727 A | 6/2001 |
| TW | I365562 A | 6/2012 |
| TW | 201228070 A1 | 7/2012 |

OTHER PUBLICATIONS

Thackeray et al., "Li2MnO3-stabilized LiMO2 (M=Mn, Ni, Co) electrodes for lithium-ion batteries," Journal of Materials Chemistry, 2007 (published online: Apr. 20, 2007), vol. 17, p. 3112-3125.

Wang et al., "Chemistry and electrochemistry of concentric ring cathode Li1.42Ni0.25Mn0.75O2+γ for lithium batteries", Journal of Materials Chemistry, vol. 22, 2012 (published online: Mar. 29, 2012), pp. 12039-12045.

Wang et al., "Growth mechanism of Ni0.3Mn0.7CO3 precursor for high capacity Li-ion Battery cathodes", Journal of Materials Chemistry, vol. 21, 2011 (published online: May 25, 2011), pp. 9290-9295.

Wu et al., "Preparation and electrochemical performance of Li-rich layered cathode material, Li[Ni0.2Li0.2Mn0.6]O2 for lithium-ion batteries," The Journal of Applied Electrochemistry, 2010 (published online: Dec. 24, 2009), vol. 40, pp. 783-789.

Taiwanese Office Action dated Sep. 23, 2014, for Taiwanese Application No. 102137075.

Chinese Office Action and Search Report, dated Jul. 13, 2016, for Chinese Application No. 201310603002.5.

* cited by examiner $Ni_{0.5}Mn_{0.5}C_2O_4 \cdot 2H_2O$
(Mn/Ni = 1)

$Co_{0.1}Ni_{0.45}Mn_{0.45}C_2O_4 \cdot 2H_2O$
(Co:Mn:Ni = 1:4.5:4.5)

Layer LiCo$_{0.1}$Ni$_{0.45}$Mn$_{0.45}$O$_2$

Spinel Li$_{0.5}$Ni$_{0.25}$Mn$_{0.75}$O$_2$

Layer-Layer $Li_{1.2}Ni_{0.4}Mn_{0.6}O_{2.2}$

NI—MN COMPOSITE OXALATE POWDER, LITHIUM TRANSITION METAL COMPOSITE OXIDE POWDER AND LITHIUM ION SECONDARY BATTERY

CROSS REFERENCE TO RELATED APPLICATIONS

This Application claims priority of Taiwan Patent Application No. 102137075, filed on Oct. 15, 2013, the entirety of which is incorporated by reference herein.

TECHNICAL FIELD

The disclosure relates to a Ni—Mn composite oxalate powder, and in particular to a Ni—Mn composite oxalate powder that may be calcined with a lithium salt to form a lithium transition metal composite oxide powder for use as a positive electrode material in lithium ion batteries.

BACKGROUND

Along with the rapid development and availability of portable electronic products, demand for lithium-ion (Li-ion) secondary batteries is increasing due to their remarkable advantages, such as light weight, high operating voltage, high energy density, long service life and so on. In addition, Li-ion secondary batteries are more environmentally friendly when compared to nickel-cadmium, nickel-hydrogen and nickel-zinc batteries and are touted as the leading candidate for development of flexible batteries.

Among various cathode materials, the class of layered composite oxides, expressed as $xLi_2MnO_3 \cdot (1-x)Li(NiMn)O_2$ (LMO), has drawn escalated attention due to their high capacities beyond 250 mAh/g. This class of cathode materials may produce a theoretical specific energy of above 1000 Wh/kg, much higher than that of $LiMn_2O_4$, $LiFePO_4$ and $Li[NiCoMn]O_2$.

In addition to the inherent properties of materials per se, the microstructure of materials can have an impact on the performance of batteries, such as energy density and discharge power. Moreover, the crystal structure of the material powder is influential to the migration of lithium ions during battery charge/discharge. The migration of lithium ions usually occurs at crystal planes (101) and (104), while the diffusion of lithium ions usually occurs at crystal plane (103), which makes it possible to alter the crystal lattice to increase the space for lithium ion migration. There remains a need in the art to improve the cathode materials in various aspects to improve performance of Li-ion batteries (also referred to as "Li batteries").

SUMMARY

In one aspect, the disclosure provides a Ni—Mn composite oxalate powder, comprising a plurality of biwedge octahedron particles represented by a general formula: $Ni_qMn_xCo_yM_zC_2O_4 \cdot nH_2O$, wherein $q+x+y+z=1$, $0<q<1$, $0<x<1$, $0\le y<1$, $0\le z<0.15$, $0\le n\le 5$, and M is at least one of Mg, Sr, Ba, Cd, Zn, Al, Ga, B, Zr, Ti, Ca, Ce, Y, Nb, Cr, Fe and V.

In another aspect, the disclosure also provides a lithium transition metal composite oxide powder, comprising a plurality of biwedge octahedron particles represented by a general formula: $Li_aNi_bMn_cCo_dM_eO_f$, wherein $0.5\le a\le 2$, $b+c+d+e=1$, $0<b<1$, $0<c<1$, $0\le d<1$, $0\le e<0.15$, $2\le f\le 3$, and M is at least one of Mg, Sr, Ba, Cd, Zn, Al, Ga, B, Zr, Ti, Ca, Ce, Y, Nb, Cr, Fe and V.

In a further aspect, the disclosure provides a lithium ion battery, comprising a positive electrode, a negative electrode and a separator disposed between the positive electrode and negative electrode, and an electrolyte in the separator, wherein the positive electrode contains the above lithium transition metal composite oxide powder as an active material of the positive electrode.

A detailed description is given in the following embodiments with reference to the accompanying drawings.

BRIEF DESCRIPTION OF DRAWINGS

The present invention can be more fully understood by reading the subsequent detailed description and examples with references made to the accompanying drawings, wherein.

DETAILED DESCRIPTION

The following description is of the best-contemplated mode of carrying out the invention. This description is made for the purpose of illustrating the general principles of the invention and should not be taken in a limiting sense. The scope of the invention is best determined by reference to the appended claims.

This disclosure provides a Ni—Mn composite oxalate powder composed of a plurality of biwedge octahedron particles of substantially equal size. The powder may be further calcined with a lithium salt to form a lithium transition metal composite oxide powder, also composed of biwedge octahedron particles, for use as a positive electrode material in lithium-ion batteries. The resulting electrode can provide a shorter distance for lithium ions to diffuse into and out from the material, thus improving the first cycle discharge capacity and large-current discharge ability.

Figure 1:
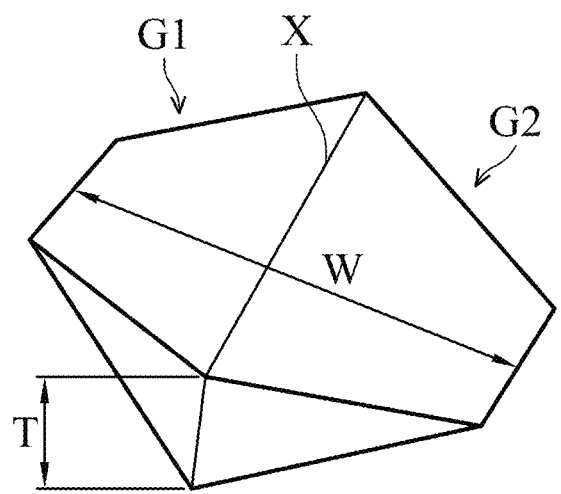
FIG. 1 is a schematic view of a biwedge octahedron particle of the disclosure.

FIG. 1 illustrates a biwedge octahedron particle of the disclosure. The particle of the disclosure has a biwedge octahedron shape, which is symmetrical along its central-ridge X, and each of the left half portion G1 and the right half portion G2 can be regarded as a wedge structure with narrow top and wide bottom. This particular octahedron structure is referred to as "biwedge octahedron" in this disclosure to distinguish over the common bipyramid octahedron.

The present disclosure provides a Ni—Mn composite oxalate powder including a plurality of biwedge octahedron particles represented by a general formula: $Ni_qMn_xCo_yM_zC_2O_4 \cdot nH_2O$, wherein $q+x+y+z=1$, $0<q<1$, $0<x<1$, $0 \leq y<1$, $0 \leq z<0.15$, $0 \leq n \leq 5$, and M is at least one of Mg, Sr, Ba, Cd, Zn, Al, Ga, B, Zr, Ti, Ca, Ce, Y, Nb, Cr, Fe and V.

In one embodiment, the Ni—Mn composite oxalate powder only contains metallic elements of Ni and Mn (namely, $y=z=0$). In another embodiment, it further contains Co (y is not zero), giving a Ni—Mn—Co composite oxalate powder. In either case, a minor amount of other metals (typically $z<0.15$) such as Mg, Sr, Ba, Cd, Zn, A, Ga, B, Zr, Ti, Ca, Ce, Y, Nb, Cr, Fe, V or a combination thereof may be included in the powder. For the sake of brevity, the Ni—Mn composite oxalate powder, the Ni—Mn—Co composite oxalate powder, and the Ni—Mn or Ni—Mn—Co composite oxalate powder that contains additional metals are all referred to as a "Ni—Mn composite oxalate powder". The Ni—Mn composite oxalate powder may include 0-5, typically 1-4, crystal waters, depending on the composition of oxalate powders.

The Ni—Mn composite oxalate powder of present disclosure may be synthesized by co-precipitation. Ni salt, Mn salt and optionally Co salt and/or other metal salts are added to an oxalic acid solution at a preselected ratio, and the pH value of the solution is then adjusted to 4-8 by ammonia water, followed by mixing at suitable temperature, time and speed to give the desired biwedge octahedron particles.

Experiments show that the biwedge octahedron particles can be synthesized at a wide variety of metallic ratios. The SEM images of the Ni—Mn composite oxalate powder indicate that substantially all the particles contained in the powder have the biwedge octahedron structure. The average particle size of the biwedge octahedron particle may range from 0.1 µm to 20 µm, for example, 5 µm to 15 µm.

The Ni—Mn composite oxalate powder of the disclosure includes biwedge octahedron particles of a specific width (W) to thickness (T) ratio (W/T), for example 1.5-6.7. In one embodiment, at least more than 70% of the biwedge octahedron particles in the powder have the width to thickness (W/T) ratio of 1.8 to 6.3.

The present disclose further provides a lithium transition metal oxide powder including a plurality of biwedge octahedron particles represented by a general formula: $Li_aNi_bMn_cCo_dM_eO_f$, wherein $0.5 \leq a \leq 2$, $b+c+d+e=1$, $0<b<1$, $0<c<1$, $0 \leq d<1$, $0 \leq e<0.15$, $2 \leq f \leq 3$, and M is at least one of Mg, Sr, Ba, Cd, Zn, Al, Ga, B, Zr, Ti, Ca, Ce, Y, Nb, Cr, Fe and V.

The lithium transition metal composite oxide powder of the present disclosure may be prepared by calcining the Ni—Mn composite oxalate powder and a lithium salt. The resulting particles still have the biwedge octahedron shape. In one embodiment, the lithium transition metal composite oxide powder only contains metallic elements of Li, Ni and Mn (namely, $d=e=0$), giving a Li—Ni—Mn composite oxide powder. In another embodiment, it may be further include Co (d is not zero), giving a Li—Ni—Mn—Co composite oxide powder. In either case, the Li—Ni—Mn composite oxide powder or Li—Ni—Mn—Co composite oxide powder may further include a minor amount of one or more other metals ($e<0.15$) such as Mg, Sr, Ba, Cd, Zn, Al, Ga, B, Zr, Ti, Ca, Ce, Y, Nb, Cr, Fe, or V. Altering the type of component metal amounts thereof may result in improvements on structural stability of layered oxide, thereby increasing service life in electrochemical cycles. The incorporation of minor metals and the process thereof can be found in U.S. Pat. No. 7,205,072, the disclosure of which is incorporated herein in its entirety, but the invention is not limited thereto.

For the sake of brevity, the above-mentioned oxide powders are all referred to as a "lithium transition metal composite oxide powder". The SEM image shows that the particles remain in the biwedge octahedron shape after being subjected to calcination with a lithium salt. The biwedge octahedron particles of the lithium transition metal composite oxide powder has an average particle size ranging from 1 µm to 25 µm, such as 5 µm to 20 µm, or 5 µm to 12 µm. In one embodiment, the Ni—Mn composite oxalate powders may be mixed with a Li salt, such as $Li_2CO_3$, heated at 300° C.-500° C. in air, and then calcined at a higher temperature, such as 800° C.-1200° C. The crystalline phase of the resulting powder is determined by the calcination conditions and the composition of metals. The crystal structure may include spinel-type, layered-layered, or layered crystal structures. In spite of the different crystal structures, the particles of lithium transition metal composite oxide powder are in the biwedge octahedron shape.

The particles of lithium transition metal composite oxide powder are further characterized by a plurality of trenches on their surfaces. The trenches are substantially uniformly distributed throughout the entire surface of the particle, and typically have a width ranging from 80 to 350 nm, for example, from 100 to 300 nm. Since these trenches are distributed over the exterior surface of the particles, they significantly increase the solid/electrolyte contact surface area, even if the total pore volume may be small. The total porous volume of the lithium transition metal composite oxide powder may be in a range of 0.001 to 0.02 $cm^3/g$.

The lithium transition metal composite oxide powder of the disclosure may be used as (but not limited to) electrode active materials for lithium ion batteries. The resulting battery exhibits improved first cycle discharge capacity and large-current discharge ability. This result may be attributed to the flat shape of the particles, the shorter Li-diffusion pathway, and the larger solid/electrolyte contact area due to the surface trenches.

The lithium transition metal composite oxide powder also has a specific width (W) to thickness (T) ratio (W/T), typically ranging from 1.5 to 4.6. In one embodiment, at least more than 70% of the particles of the lithium transition metal composite oxide powder have a width-to-thickness ratio (W/T) of 1.5-4.6. The biwedge octahedron particles may be doped with sulfur or fluorine to form sulfur oxide or oxyfluoride. The doping of fluorine can reduce impedance, improve stability of the layered oxide structure during electrochemical cycling, and increase the reversible capacity while preserving the other electrochemical performance features, as described in U.S. Pat. No. 7,205,072 and US20080157027, for example. The sulfur dopant can improve surface properties of the electrode and cause beneficial properties of the battery, such as improved storage properties and better safety, as described in WO2009021651. The contents of each of the references discussed herein, including the references cited therein, are incorporated by reference in their entirety.

The lithium transition metal composite oxide powder may optionally contain a protective layer on the surface of the biwedge octahedron particles to prevent the electrode particles from dissociation during charge/discharge, thereby protecting the electrode from capacity loss effects, such as dissolution and oxygen loss during electrochemical cycling of the cells. The protect layer may include fluorine, sulfur, metal fluoride, metal hydroxide, metal oxide, or a combination thereof. Examples of the metal oxide or metal hydroxide may include $ZrO_2$, $Al_2O_3$, MgO, AlOOH, TiO, $TiO_2$, $Y_2O_3$ and $SiO_2$. Examples of the metal fluorine may include CsF, KF, LiF, NaF, RbF, TiF, AgF, $AgF_2$, $BaF_2$, $CaF_2$, $CuF_2$, $CdF_2$, $FeF_2$, $HgF_2$, $Hg_2F_2$, $MnF_2$, $MgF_2$, $NiF_2$, $PbF_2$, $SnF_2$, $SrF_2$, $XeF_2$, $ZnF_2$, $AlF_3$, $BF_3$, $BiF_3$, $CeF_3$, $CrF_3$, $DyF_3$, $EuF_3$, $GaF_3$, $GdF_3$, $FeF_3$, $HoF_3$, $InF_3$, $LaF_3$, $LuF_3$, $MnF_3$, $NdF_3$, $VOF_3$, $PrF_3$, $SbF_3$, $ScF_3$, $SmF_3$, $TbF_3$, $TiF_3$, $TmF_3$, $YF_3$, $YbF_3$, $TiF_3$, $CeF_4$, $GeF_4$, $HfF_4$, $SiF_4$, $SnF_4$, $TiF_4$, $VF_4$, $ZrF_4$, $NbF_5$, $SbF_5$, $TaF_5$, $BiF_5$, $MoF_5$, $ReF_5$, $SF_5$, and $WF_5$. The manufacture of a protective layer for electrodes can be found in US 20040191633, US 20080157027, US 20080157027, CA 2694000A1, WO 2009021651A1, US 20090087362, but the invention is not limited thereto. The contents of each of the references discussed herein, including the references cited therein, are incorporated by reference in their entirety.

The lithium transition metal composite oxide powder of present disclosure may be used as active materials of the positive electrode. For example, the lithium transition metal composite oxide powder is mixed with a conductive additive and a binder in a solvent to form a cathode paste composition. The lithium transition metal composite oxide powder, the conductive additive and the binder may be present in a weight ratio of 80-93:0.1-5:0.1-5, such as 91:6:3. Furthermore, the lithium transition metal composite oxide powder may be mixed with 5%-10% of other materials, or particles of other shapes (spherical, rod, and so on) to form the cathode paste composition.

The conductive additive may include, but is not limited to, carbon black, graphite, acetylene black, nickel powder, aluminum powder, titanium powder, stainless steel powder and a combination thereof. The binder may serve to improve the mechanical properties of the electrode. Suitable binder may include polyvinylidene fluoride (PVDF), styrene-butadiene rubber (SBR), polyamide, melamine resin and a combination thereof. Suitable solvents for forming the cathode paste composition include, but are not limited to, γ-butyrolactone, propylene carbonate, and N-methyl pyrolidone (NMP), singly or admixture with one another to provide a co-solvent system. In addition, the cathode paste composition may optionally include other additives such as a surfactant, an initiator, and so on. The cathode paste composition can be coated on a metal foil, for instance aluminum foil, and then dried, and roller milled to form a modified positive electrode plate.

Figure 12:
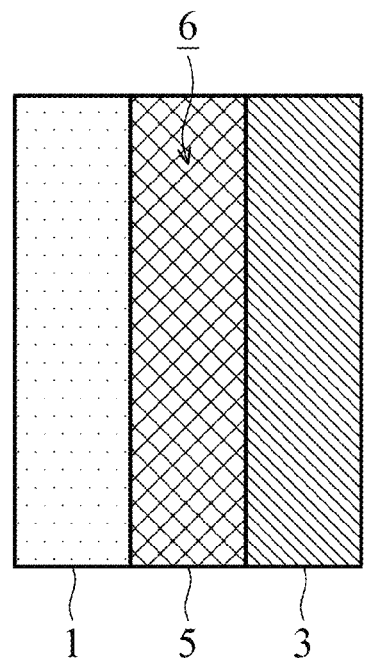
FIG. 12 is schematic view of a lithium ion secondary battery of the disclosure.

FIG. 12 shows a schematic cross section of a lithium ion battery of the present disclosure. The lithium ion battery includes a positive electrode plate 1, a negative electrode plate 3, and a separator 5 disposed there between. The separator 5 contains an electrolyte therein. The positive electrode plate includes the lithium transition metal composite oxide powder of the disclosure.

The negative electrode plate 3 may include carbonaceous material and lithium alloy. Examples of the carbonaceous materials include carbon particles, graphite, hard carbon, soft carbon, carbon fiber, carbon nano-tube or a combination thereof. In one embodiment, the carbonaceous particles have particle sizes ranging from 1 μm to 30 μm. The negative electrode may be Al, Zn, Bi, Cd, Sb, Si, Pb, Sn, $Li_3FeN_2$, $Li_{2.6}Co_{0.4}N$, $Li_{2.6}Cu_{0.4}N$, or a combination thereof. In addition, the negative electrode may further include metal oxide, such as SnO, $SnO_2$, GeO, $GeO_2$, $In_2O$, $In_2O_3$, PbO, $PbO_2$, $Pb_2O_3$, $Pb_3O_4$, $Ag_2O$, AgO, $Ag_2O_3$, $Sb_2O_3$, $Sb_2O_4$, $Sb_2O_5$, SiO, ZnO, CoO, NiO, FeO, $TiO_2$, $Li_3Ti_5O_{12}$ or a combination thereof. The negative electrode may include a binder, such as polyvinylidene fluoride (PVDF), styrene-butadiene rubber (SBR), polyamide, melamine resin or a combination thereof.

The described separator 5 is an insulating material, such as polyethylene (PE), polypropylene (PP), or a multi-layered structure thereof such as PE/PP/PE. The major components of the described electrolyte are organic solvent, lithium salt, and additives. The organic solvent can be γ-butyrolactone (GBL), ethylene carbonate (EC), propylene carbonate (PC), diethyl carbonate (DEC), propyl acetate (PA), dimethyl carbonate (DMC), ethylmethyl carbonate (EMC), or combinations thereof. The lithium salt can be $LiPF_6$, $LiBF_4$, $LiAsF_6$, $LiSbF_6$, $LiClO_4$, $LiAlCl_4$, $LiGaCl_4$, $LiNO_3$, $LiC(SO_2CF_3)_3$, $LiN(SO_2CF_3)_2$, LiSCN, $LiO_3SCF_2CF_3$, $LiC_6F_5SO_3$, $LiO_2CCF_3$, $LiSO_3F$, $LiB(C_6H_5)_4$, $LiCF_3SO_3$, $LiB(C_2O_4)_2$ or a combination thereof.

The positive electrode made from the lithium transition metal composite oxide powder of the disclosure may provide a shorter distance for lithium ions to diffuse into and out from the electrode material due to the particular particle structure, which in turn increases the first cycle discharge capacity and large-current discharge ability.

Comparative Example 1

In this example, nickel salt and manganese salt were mixed in a carbonate solution in a molar ratio of Ni:Mn=1:3 as reactants, and then the pH value of the solution was adjusted to 7.5 by ammonia water. Specifically, 6.6 g of $NiSO_4.6H_2O$, 12.7 g of $MnSO_4.H_2O$ and 10.6 g of $Na_2CO_3$ were dissolved in 1 liter of water, and then the pH value was adjusted to 7.5 by ammonia water. The solution was stirred at a speed of 600 rpm at 50° C. for 10-15 hours to allow co-precipitation of the nickel, manganese and carbonate ions. After filtering, washing and drying the precipitates, Ni—Mn composite carbonate ((Ni, Mn)$CO_3$) powder P was obtained, which had a uniform, spherical appearance.

Example 1

In this example, nickel salt and manganese salt were mixed in an oxalate solution in a molar ratio of Ni:Mn=1:3 as reactants, and then the pH value of the solution was adjusted to 7.5 by ammonia water. Specifically, 6.6 g of $NiSO_4.6H_2O$, and 12.7 g of $MnSO_4H_2O$ were dissolved in 1 liter of water, followed by addition of 12.6 g of $(COOH)_2.2H_2O$, 6.4 g of NaOH and 6.8 ml (28%) of ammonia water. The solution was stirred at a speed of 600 rpm at 50° C. for 30 seconds and left standing for 3 hours to allow co-precipitation of the nickel, manganese, and oxalate ions. After filtering, washing and drying the precipitates, Ni—Mn composite oxalate ($Ni_{0.25}Mn_{0.75}C_2O_4.2H_2O$)

powder A was obtained. The Ni—Mn composite oxalate powder A was composed of a plurality of biwedge octahedron particles having a particle size of about 6 μm.

Example 2

In this example, nickel salt and manganese salt were mixed in an oxalate solution in a molar ratio of Ni:Mn=2:3 as reactants, and then the pH value of the solution was adjusted to 7.5 by ammonia water. Specifically, 10.5 g of $NiSO_4.6H_2O$, and 10.1 g of $MnSO_4.H_2O$ were dissolved in 1 liter water, followed by addition of 12.6 g of $(COOH)_2.2H_2O$, 6.4 g of NaOH and 6.8 ml (28%) of ammonia water. The solution was stirred with a speed of 600 rpm at 50° C. for 30 seconds and left standing for 3 hours to allow co-precipitation of nickel, manganese, and oxalate ions. After filtering, washing and drying the precipitates, Ni—Mn composite oxalate ($Ni_{0.4}Mn_{0.6}C_2O_4.2H_2O$) powder B was obtained. The Ni—Mn composite oxalate powder B was composed of a plurality of micron-sized biwedge octahedron particles.

Example 3

In this example, nickel salt and manganese salt were mixed in an oxalate solution in a molar ratio of Ni:Mn=1:1 as reactants, and then the pH value of the solution was adjusted to 7.5 by ammonia water. Specifically, 13.1 g of $NiSO_4.6H_2O$, and 8.5 g of $MnSO_4.H_2O$ were dissolved in 1 liter water, followed by addition of 12.6 g of $(COOH)_2.2H_2O$, 6.4 g of NaOH and 6.8 ml (28%) of ammonia water. The solution was stirred with a speed of 600 rpm at 50° C. for 30 seconds and left standing for 3 hours to allow co-precipitation of nickel, manganese, and oxalate ions. After filtering, washing and drying the precipitates, Ni—Mn composite oxalate ($Ni_{0.5}Mn_{0.5}C_2O_4.2H_2O$) powder C was obtained. The Ni—Mn composite oxalate powder C was composed of a plurality of micron-sized biwedge octahedron particles.

Example 4

Figure 2A:
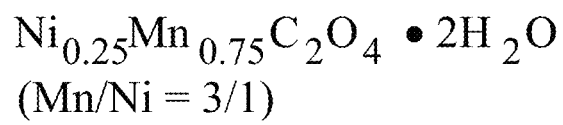
FIGS. 2a-2d are scanning electron microscope (SEM) images of Ni—Mn composite oxalate powders according to examples of the disclosure.
Figure 2A:
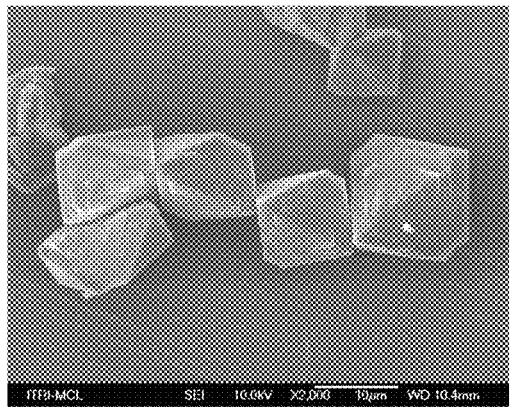
Figure 2B:
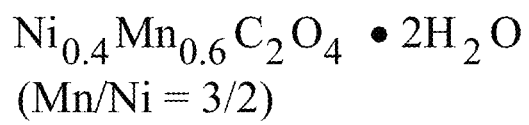
Figure 2B:
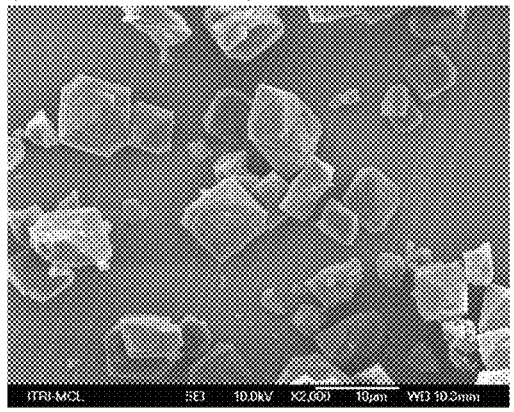
Figure 2C:
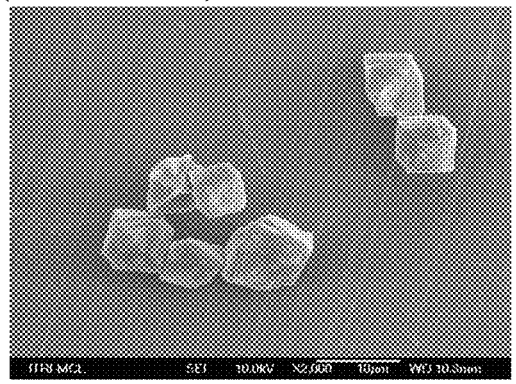
Figure 2D:
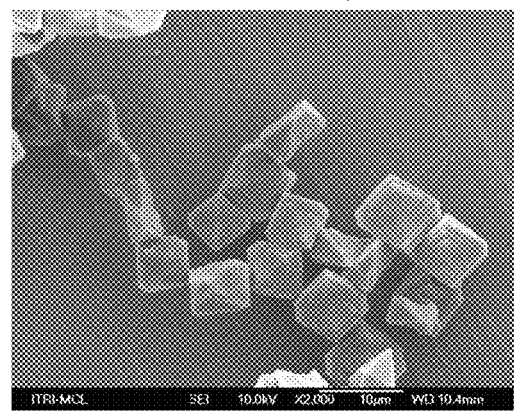
Figure 3:
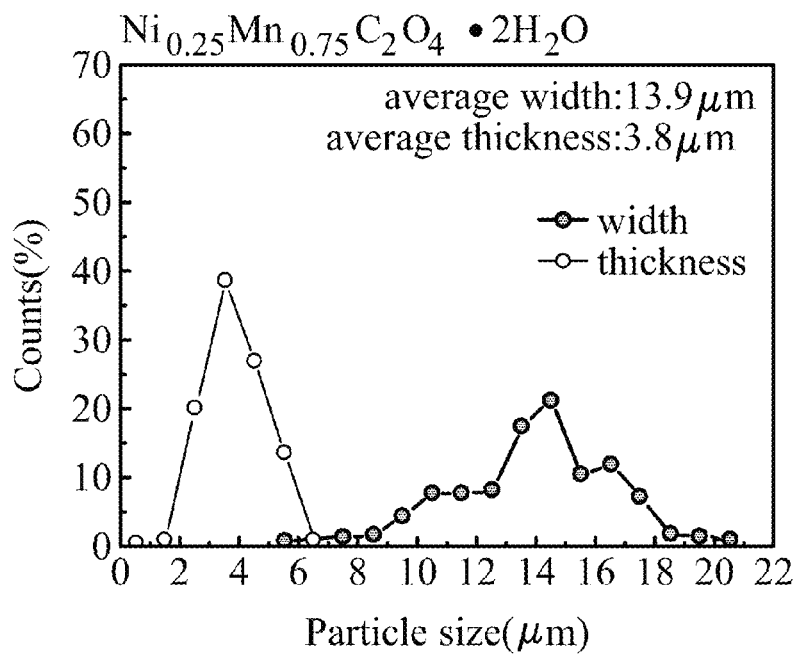
FIGS. 3a-3d are particle size distributions of Ni—Mn composite oxalate powders according to examples of the disclosure.
Figure 3:
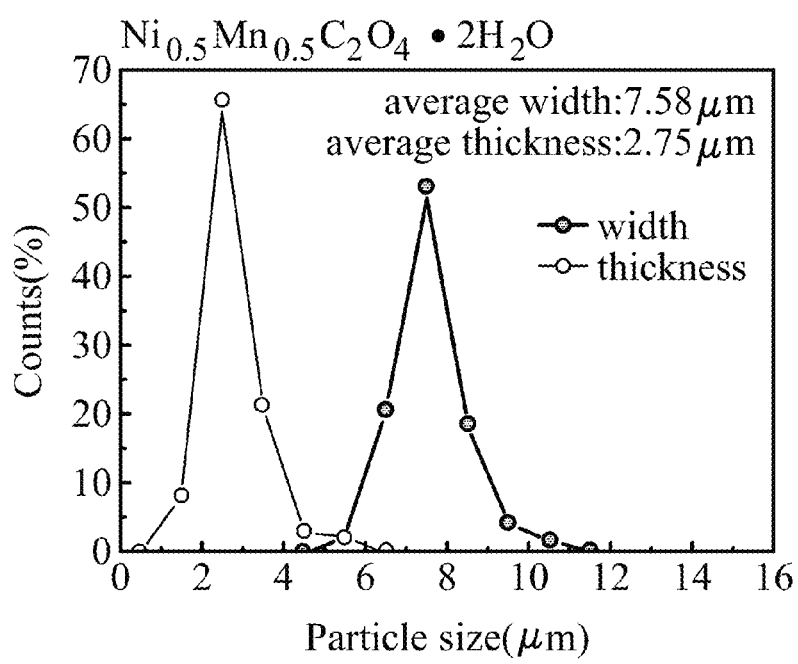
Figure 3:
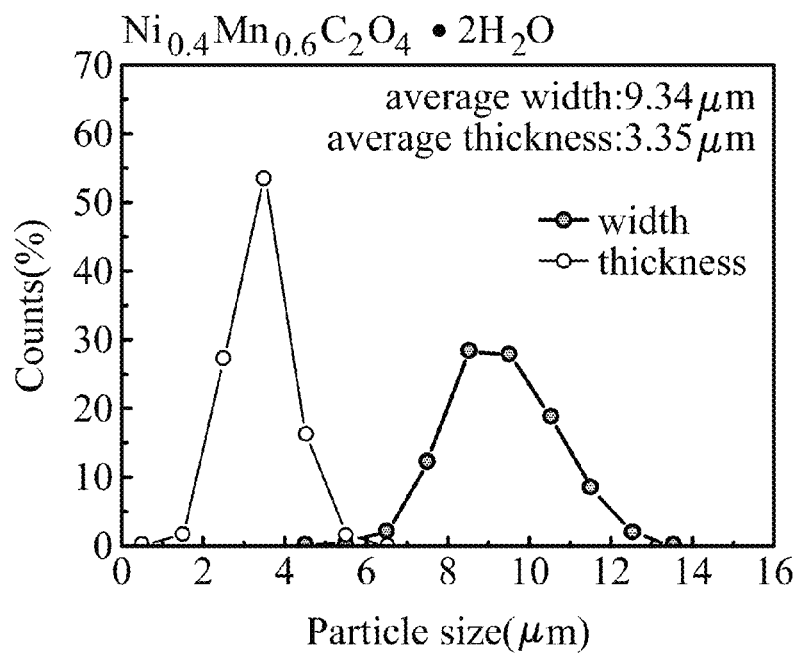
Figure 3:
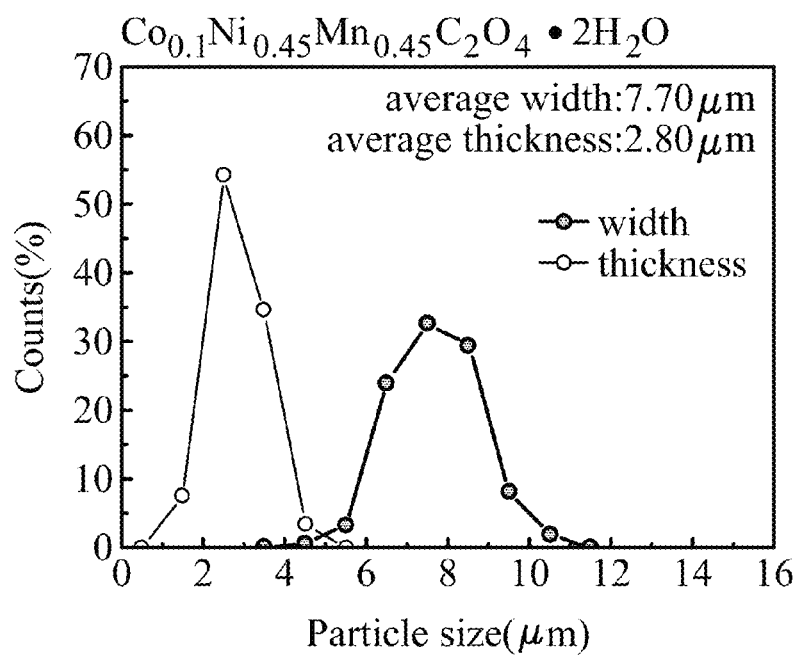

In this example, cobalt salt, nickel salt and manganese salt were mixed in an oxalate solution in a molar ratio of Co:Ni:Mn=1:4.5:4.5 as reactants, and then the pH value of the solution was adjusted to 7.5 by ammonia water. Specifically, 2.9 g of $Co(NO_3)_2.6H_2O$, 11.8 g of $NiSO_4.6H_2O$, and 7.6 g of $MnSO_4.H_2O$ were dissolved in 1 liter water, followed by addition of 12.6 g of $(COOH)_2.2H_2O$, 6.4 g of NaOH and 6.8 ml (28%) of ammonia water. The solution was stirred with a speed of 600 rpm at 50° C. for 30 seconds and left standing for 3 hours to allow co-precipitation of cobalt, nickel, manganese and oxalate ions. After filtering, washing and drying the precipitates, Co—Ni—Mn composite oxalate ($Co_{0.1}Ni_{0.45}Mn_{0.45}C_2O_4.2H_2O$) powder D was obtained. The Co—Ni—Mn composite oxalate powder D was composed of a plurality of micron-sized biwedge octahedron particles FIGS. 2a-d show a series of SEM images of the Ni—Mn composite oxalate powders of different stoichiometric ratios of Co, Ni, and Mn. FIG. 2 shows the SEM image of the Ni—Mn composite oxalate powder A of Example 1 (Ni:Mn=1:3). FIG. 2b shows the SEM image of the Ni—Mn composite oxalate powder B of Example 2 (Ni:Mn=2:3). FIG. 2c shows the SEM image of the Ni—Mn composite oxalate powder C of Example 3 (Ni:Mn=1:1). FIG. 2d shows the SEM image of the Co—Ni—Mn composite oxalate powder D of Example 4 (Co:Ni:Mn=1:4.5:4.5). As shown in the figures, the shape of particles remained unchanged as biwedge octahedron even when the Ni content was increased or additional 10% of cobalt was incorporated.

The particles size of the Ni—Mn composite oxalate powder was slightly changed with different stoichiometric ratios of metal. The crystal structure of the biwedge octahedron particles may be layer-layer, spinel-type or layered structures. The particle size distribution may be represented by the width-to-thickness ratio (W/T), which was in the range of 1.8-6.3, wherein the width-to-thickness ratio of the particles are as defined in FIG. 1. Referring to FIGS. 3a-d and Table 1, the statistics of particles size distribution of biwedge octahedron particles were calculated by SEM analysis. The width to thickness ratio (W/T) of composite oxalate particles with varying stoichiometric ratios at different percentages (10%, 25%, 75%, and 90%) was calculated, giving a W/T ratio ranging from 1.8 to 6.3. In addition, the particle width may be increased by lowering the metal concentration other than Mn. In such a case, the W/T ratio may be increased to greater than 6.3.

TABLE 1

|  | Co:Ni:Mn | W/T at 10% | W/T at 25% | W/T at 50% | W/T at 75% | W/T at 90% |
| --- | --- | --- | --- | --- | --- | --- |
| Example 1 | 0:1:3 | 6.31 | 5.05 | 3.66 | 2.81 | 2.04 |
| Example 2 | 0:2:3 | 4.29 | 3.58 | 2.79 | 2.28 | 1.77 |
| Example 3 | 0:1:1 | 4.20 | 3.41 | 2.76 | 2.35 | 1.80 |
| Example 4 | 1:4.5:4.5 | 4.36 | 3.63 | 2.80 | 2.17 | 1.80 |

Examples 5-9

The Ni—Mn composite oxalate powders A, B, C and D of Examples 1-4 were mixed with $Li_2CO_3$ in molar ratios of 1:0.75, 1:0.6, 1:0.5 and 1:0.5, respectively, and then heated in air at a rate of 5° C./min from room temperature to the selected temperature between 800 and 1000 t with a holding time between 3 and 24 hr for calcination, and then quenched. Lithium transition metal composite oxide powders A', B', C', D' and A" composed of biwedge octahedron particles of the general formula: $Li_aNi_bMn_cCo_dM_eO_f$, were thus obtained. The process conditions and compositions of the lithium transition metal composite oxide powders are summarized in Table 2, wherein the oxide powders A' and A" were both derived from the oxalate powder A with different Li ratios.

Comparative Example 2

The Ni—Mn composite carbonate powder P of comparative example was mixed with $Li_2CO_3$ in a molar ratio of 1:0.75, and then heated in air at a rate of 5° C./min from room temperature to 900° C. with a holding time of 9 hr for calcination, and then quenched. A lithium transition metal composite oxide powder P' composed of spherical particles was obtained.

TABLE 2

|  | Li:Co:Ni:Mn (molar ratio) | Composition | Calcination temperature (° C.) | Calcination time (hr) |
|---|---|---|---|---|
| Example 5 Powder A' | 6:0:1:3 | $Li_{1.5}Ni_{0.25}Mn_{0.75}O_{2.5}$ | 900 | 9 |
| Example 6 Powder B' | 6:0:2:3 | $Li_{1.2}Ni_{0.4}Mn_{0.6}O_{2.2}$ | 900 | 15 |
| Example 7 Powder C' | 2:0:1:1 | $LiNi_{0.5}Mn_{0.5}O_2$ | 900 | 15 |
| Example 8 Powder D' | 10:1:4.5:4.5 | $LiCo_{0.1}Ni_{0.45}Mn_{0.45}O_2$ | 1000 | 20 |
| Example 9 Powder A'' | 2:0:1:3 | $Li_{0.5}Ni_{0.25}Mn_{0.75}O_2$ | 800 | 3 |
| Comparative Example 2 Powder P' | 6:0:1:3 | $Li_{1.5}Ni_{0.25}Mn_{0.75}O_{2.5}$ (sphere) | 900 | 9 |

Figure 4:
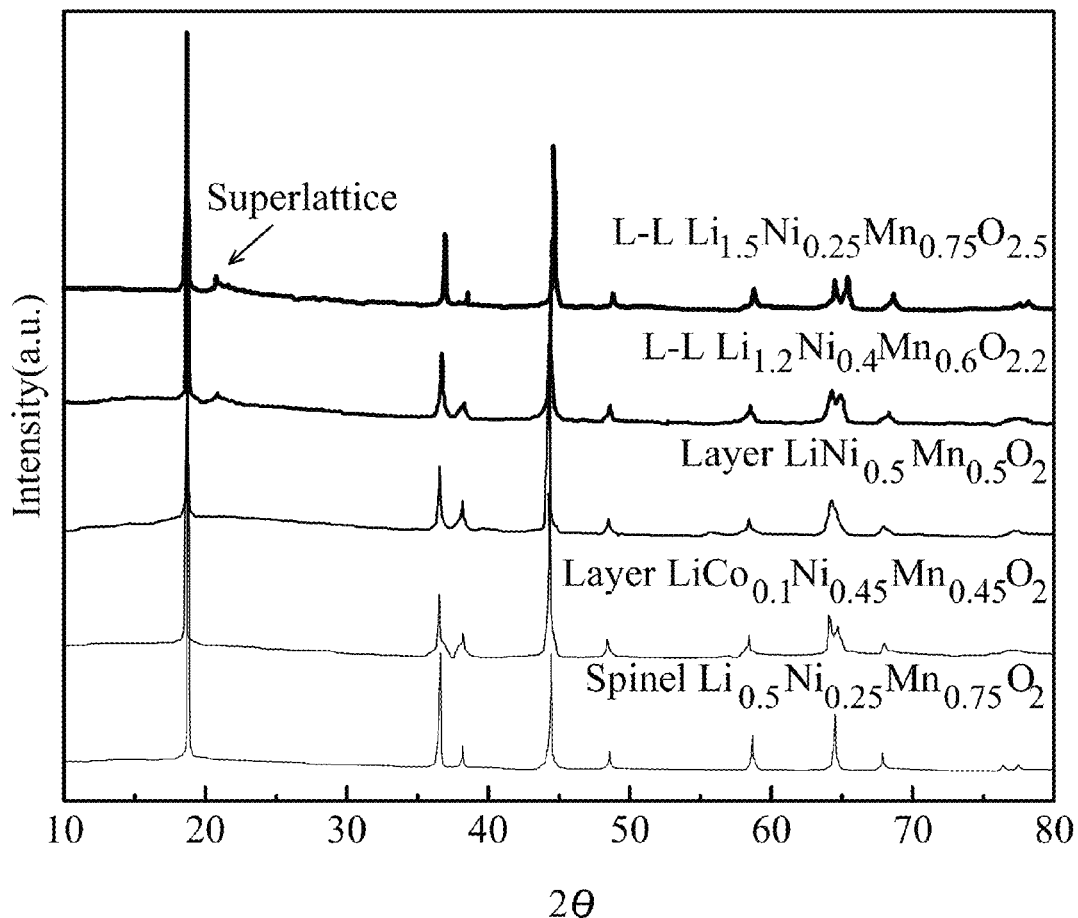
FIG. 4 shows X-ray diffraction (XRD) patterns of Ni—Mn composite oxide powders according to examples of the disclosure.
Figure 5A:
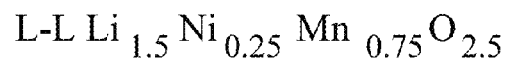
FIGS. 5a-5e are SEM images of lithium transition metal composite oxide powders according to examples of the disclosure.
Figure 5A:
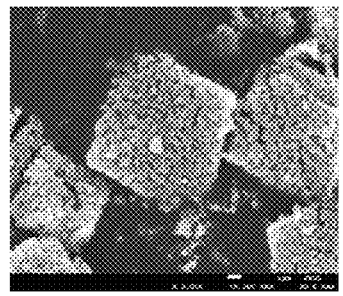
Figure 5B:
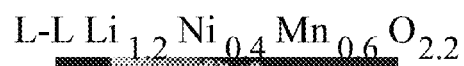
Figure 5B:
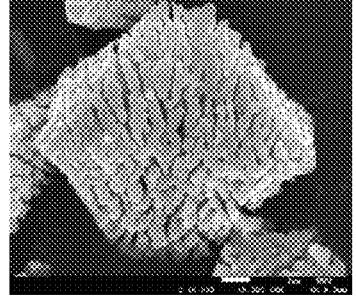
Figure 5C:
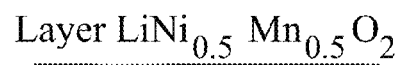
Figure 5C:
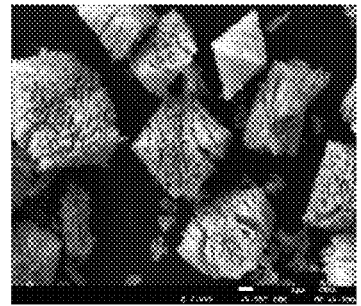
Figure 5:
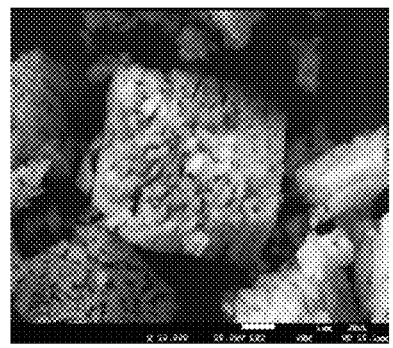
Figure 5:
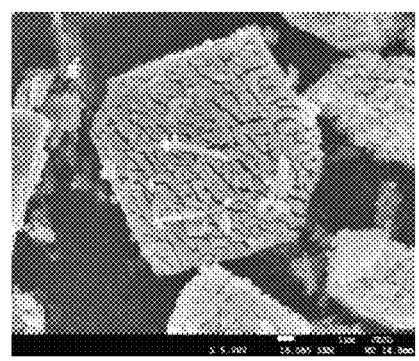

FIG. 4 shows the X-ray diffraction (XRD) pattern of the above lithium transition metal composite oxide powders. Adjusting the ratio of Ni, Mn, or Co of the lithium transition metal composite oxide powder may result in different crystal structures, such as the layer-layer structure of $Li_{1.5}Ni_{0.25}Mn_{0.75}O_{2.5}$(Powder A') and $Li_{1.2}Ni_{0.4}Mn_{0.6}O_{2.2}$ (Powder B') in Examples 5-6, the layer structure of $LiNi_{0.5}Mn_{0.5}O_2$(Powder C') and $Li_{0.1}Co_{0.1}Ni_{0.45}Mn_{0.75}O_2$ (Powder D') in Examples 7-8, and the spinel-type structure of $Li_{0.5}Ni_{0.25}Mn_{0.75}O_2$ (PowderA'') in Example 9. The layer-layer structure of lithium transition metal composite oxide showed diffraction peaks (20) between 20° and 30°, representing the existence of a superlattice. FIGS. 5(a)-5(e) are SEM pictures of the Powders A', B', C', D', and A'', which all exhibit biwedge octahedron structures irrespective of their crystal structures.

Figure 6:
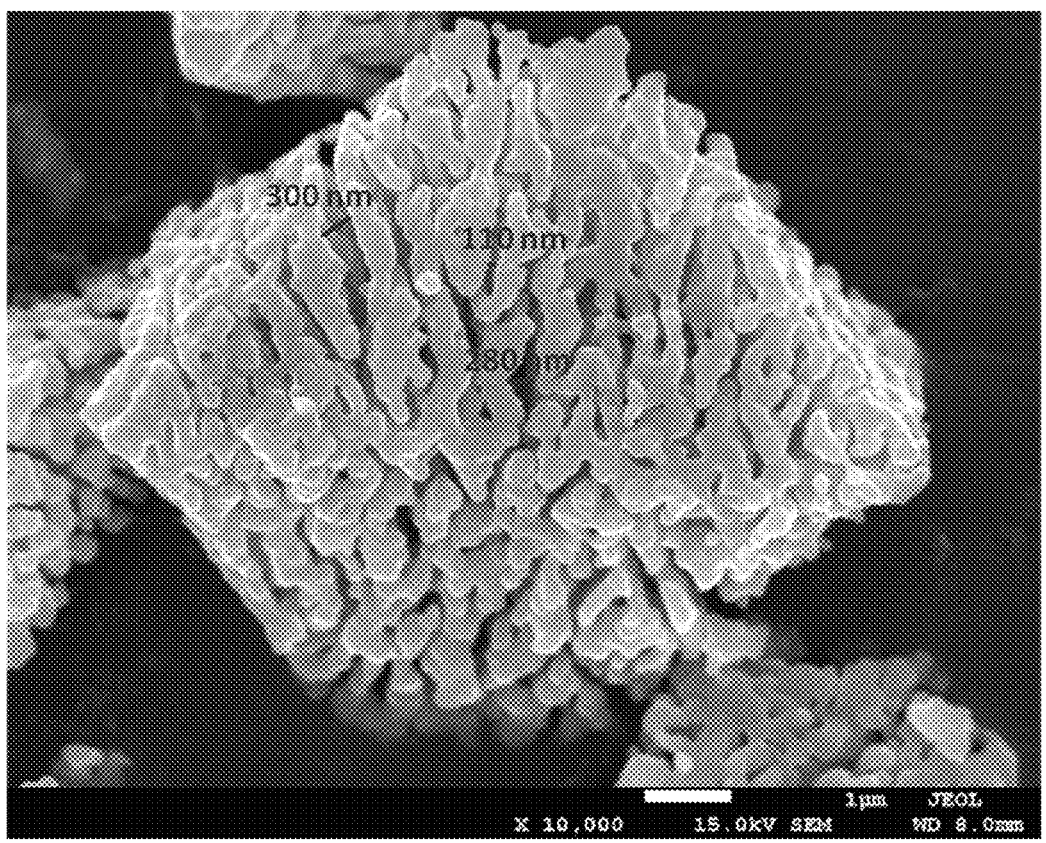
FIG. 6 is a SEM image of a lithium transition metal composite oxide powder of examples of the disclosure.

FIG. 6 is a magnified SEM image showing the surface structure of the lithium transition metal composite oxide particle. As can be seen, a plurality of trenches were formed on the particle surface. These surface trenches had a width of 100-300 nm and were substantially distributed throughout the entire surface of the particle.

The statistics of particles size distribution of Powders A', B', C' were calculated by SEM analysis. The width to thickness ratio (W/T) of lithium transition metal composite oxide powders with varying stoichiometric ratios at different percentages (10%, 25%, 50%, 75%, and 90%) was calculated, giving a W/T ratio ranging from 1.5 to 4.6. The results are listed in Table 3 below. The average particles size was 13.2 μm.

TABLE 3

|  | Li:Co:Ni:Mn (molar ratio) | W/T at 10% | W/T at 25% | W/T at 50% | W/T at 75% | W/T at 90% |
|---|---|---|---|---|---|---|
| Example 5 Powder A' | 6:0:1:3 | 4.56 | 3.58 | 2.75 | 2.15 | 1.68 |
| Example 6 Powder B' | 6:0:2:3 | 4.10 | 3.29 | 2.48 | 1.91 | 1.49 |
| Example 7 Powder C' | 2:0:1:1 | 3.39 | 2.74 | 2.17 | 1.77 | 1.47 |

Figure 7:
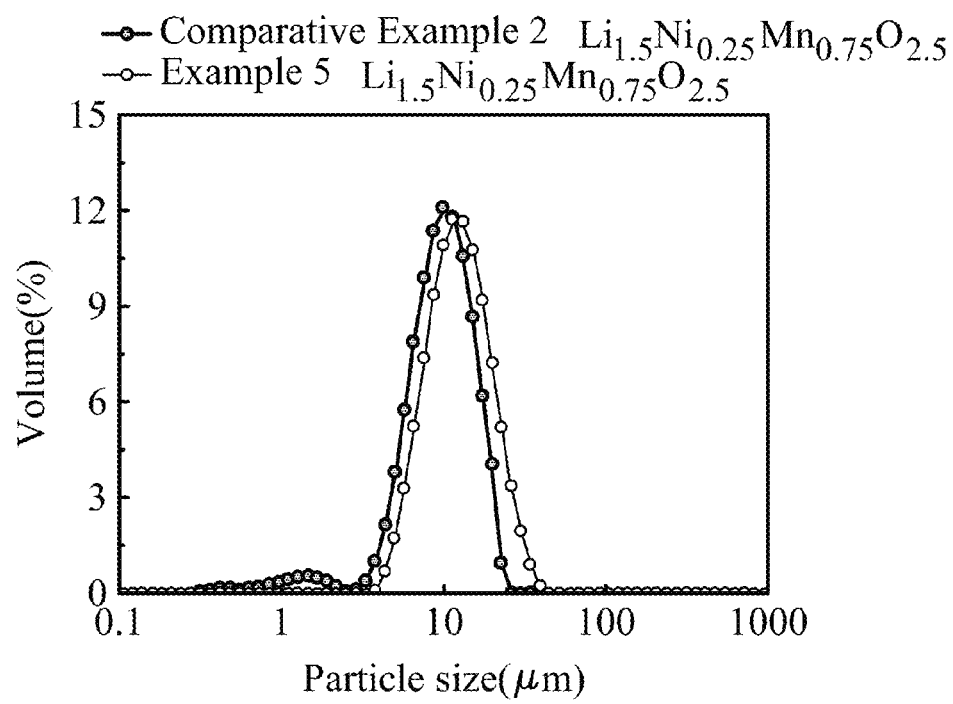
FIG. 7 compares particle size distributions of lithium transition metal composite oxide powders of Comparative Example 2 and Example 5.

FIG. 7 shows the particle distribution and average particle size analysis by particle size analyzer with static light scattering method. The spherical powder P' had an average particle size ($D_{50}$) of 10.5 μm, while the biwedge octahedron powder A' had a larger average particle size ($D_{50}$) of 13.2 μm. It was surprising and unexpected that the biwedge octahedron powder exhibited better discharge rate performance than spherical powder, since it is generally recognized that a smaller particle size would result in better discharge rate performance. This unexpected effect may be attributed to the flat shape of biwedge octahedron particles, the shorter Li-ion diffusion pathway, and the larger solid/electrolyte contact area due to the surface trenches.

C-Rate Discharge Test

A positive electrode plate was prepared from a paste containing 80% of the biwedge octahedron powder A' of Example 5, 8% of graphic flake (KS6 from Timcal Corp.), 4% of carbon black (Super P from Timcal Corp.) and 8% of binder (PVDF). A coin cell consisting of the above prepared positive electrode, a Li foil disk as the counter electrode, and electrolyte of 1M $LiPF_6$ in a 1:2 v/v mixture of ethylene carbonate (EC) and dimethyl carbonate (DMC) was assembled. A comparative coin cell was prepared by repeating the same procedure except that the powder A' was replaced by the spherical powder P' of Comparative Example 2.

Figure 8:
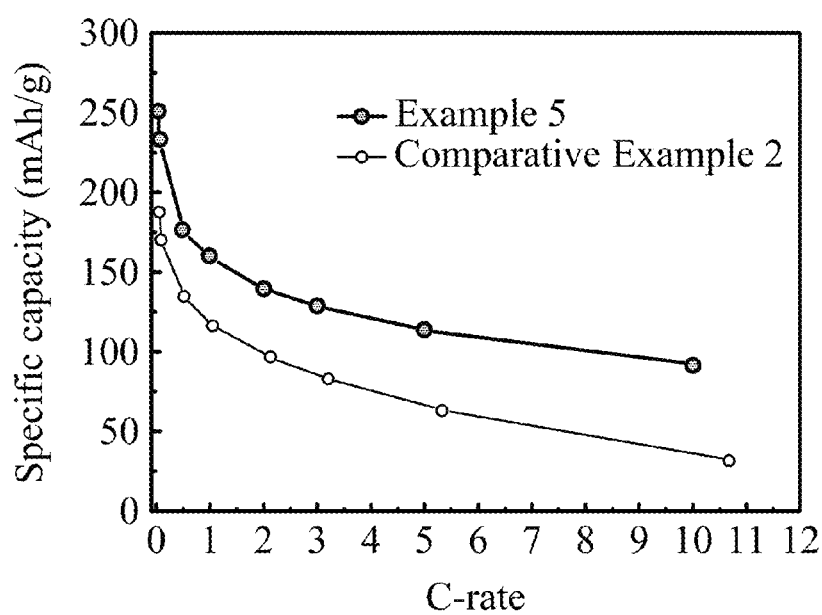
FIG. 8 compares capacities at different C-rates between the coin cells with the biwedge octahedron powder of Example 5 and the spherical powder of Comparative Example 2.

Afterwards, a C-rate discharge test was performed to compare the variation of the specific capacity under different charging current rates. As shown in FIG. 8, the coin cell with the biwedge octahedron powder A' exhibited a specific capacity of 160 mAh/g for the 1 C-rate, and a specific capacity of 140 mAh/g for the 2C-rate, significantly higher than those of the coin cell with the spherical powder P'. The difference in specific capacity was even more obvious above 2C-rate. Accordingly, the battery with the biwedge octahedron particles of the disclosure has a higher capacity at high current rate.

The average particle size, specific surface area and pore volume of the biwedge octahedron powder A' and spherical powder P' were measured and the results are listed in Table 4. The biwedge octahedron powder A' has an obviously smaller specific surface area than the spherical powder P'. In addition, the biwedge octahedron powder A' has a larger average particle size and a smaller total pore volume as compared to the spherical powder P'.

Figure 9:
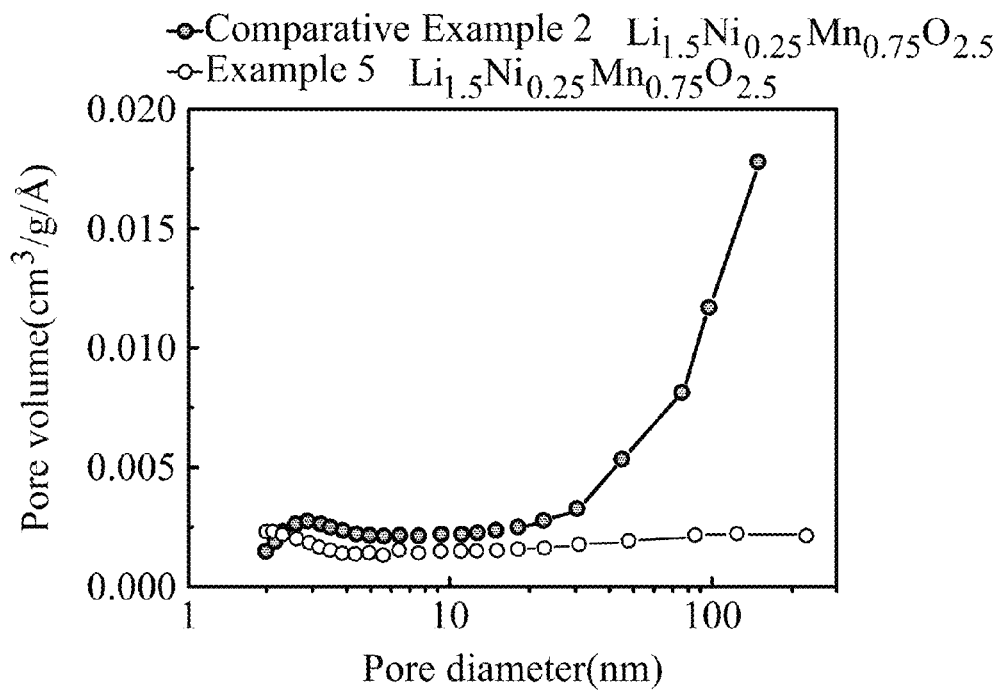
FIG. 9 compares the pore size distributions of the biwedge octahedron powder of Example 5 and the spherical powder of Comparative Example 2.

FIG. 9 shows a graph of pore diameter vs. pore volume for powders A' and P', which may be used to indicate powder density. As shown in the figure, the pore volume of the biwedge octahedron powder A' only had a slight change in relation to the pore diameter, while the pore volume of the spherical powder P' significantly increased with the pore diameter, indicating that the biwedge octahedron powder A' has a denser structure than the spherical powder P'. This result was also surprising, since it is generally recognized that a looser structure should facilitate the migration of lithium ions, and provide an increased discharge performance. However, in the C-rate test, the powder A' exhibited a higher capacity at high current rate, which may be attributed to the biwedge octahedron structure.

TABLE 4

| $Li_{1.5}Mn_{0.75}Ni_{0.25}O_{2.5}$ | $D_{50}$ (μm) | Total pore volume ($cm^3/g$) by BET-BJH |
|---|---|---|
| Example 5: Powder A' | 13.2 | 0.0041 |
| Comparative Example 2: Powder P' | 10.5 | 0.0101 |

Charge/Discharge Capacity Evaluation

Charge/discharge capacity evaluations of the lithium metal oxide electrodes were performed on coin cells by the following procedures.

Figure 10:
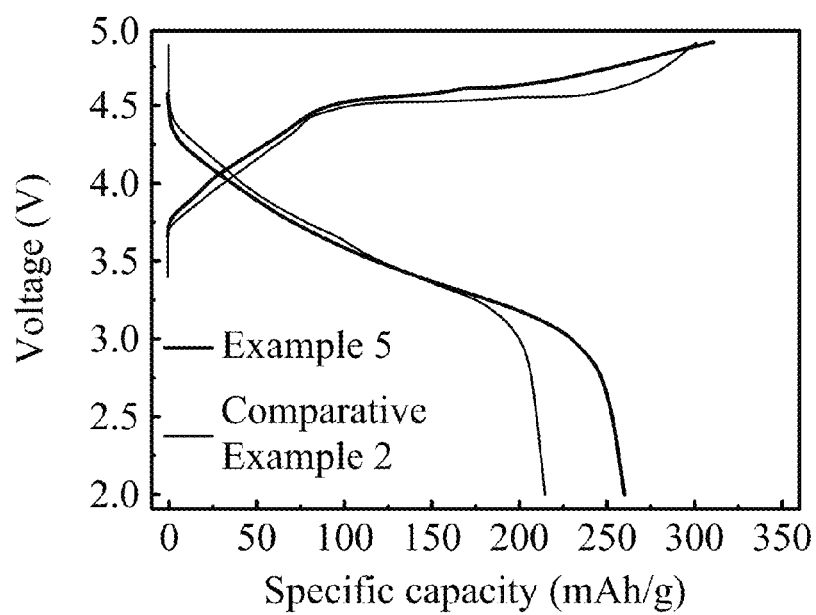
FIGS. 10a-10c are charge/discharge voltage profiles for electrodes made of the biwedge octahedron powder of Examples 5, 6, and 9 and the spherical powder of Comparative Example 2.
Figure 10:
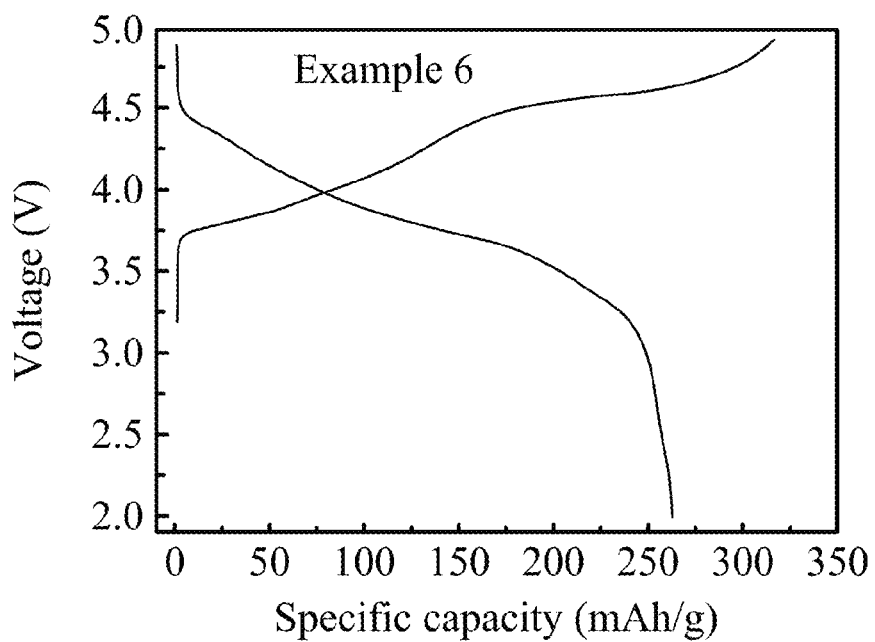
Figure 10:
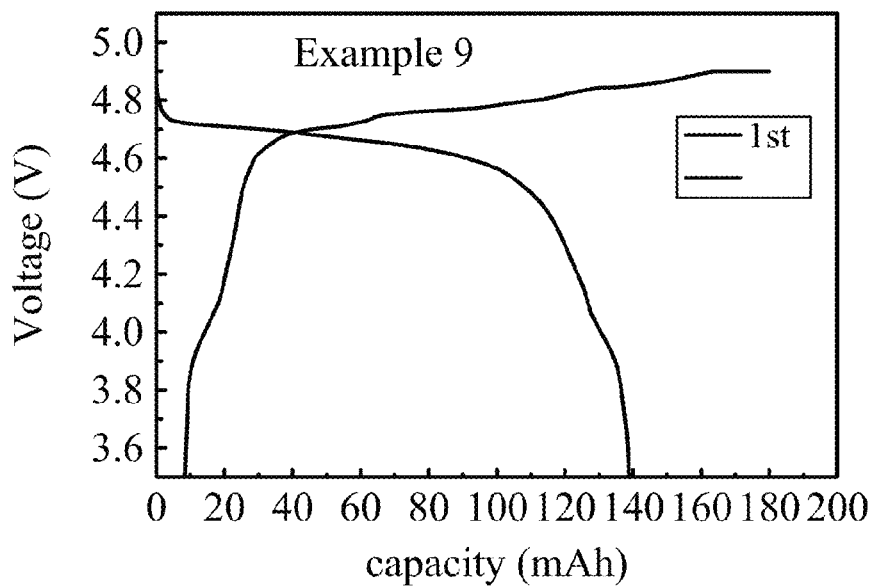

A positive electrode plate was prepared from a paste containing 80% of the biwedge octahedron powder A' of Example 5, 8% of graphite flake, 4% of carbon black and 8% of binder (PVDF). A coin cell consisting of the above prepared positive electrode, a Li foil disk as the counter electrode, and electrolyte of 1M $LiPF_6$ in a 1:2 v/v mixture of ethylene carbonate (EC) and dimethyl carbonate (DMC) was assembled. The same procedure was repeated for making coin cells containing the powders A", B', and P'. The cells were charged and discharged between 2.0 and 4.9 V using a current density of 0.1 C for the first cycle, and the results are listed in Table 5 and shown in FIGS. 10a-c. As can be seen, the cells containing the biwedge octahedron powders A', A", B' all showed a smaller first-cycle irreversible capacity than that containing the spherical powder P'.

TABLE 5

| | First charge cycle (mAh/g) | First discharge cycle (mAh/g) | First charge/discharge cycle irreversible capacity (0.1 C/0.1 C) (%) |
|---|---|---|---|
| Example 5: Powder A' | 310.44 | 260.37 | 16.13 |
| Example 6: Powder B" | 316.96 | 266.57 | 15.90 |
| Example 9: Powder A" | 180.87 | 138.96 | 23.17 |
| Comparative Example 3: Powder P' | 301.07 | 214.82 | 28.65 |

Cycle Life

Figure 11:
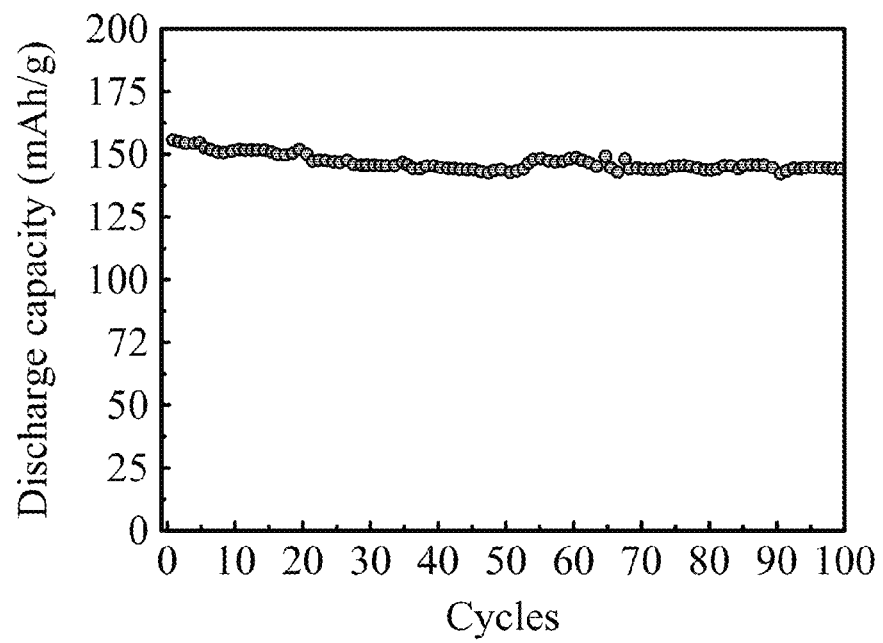
FIG. 11 is a cycle life curve of an electrode made of lithium transition metal composite oxide powder of the disclosure.

FIG. 11 shows a plot of the specific capacity vs. cycle number of the coin cell containing the powder A'. The coin cell was charged and discharged between 2 V and 4.6 V at room temperature using a current of 1 C to test the cycle life. As shown in the figure, no significant decay was observed after 100 cycles.

While the disclosure has been described by way of example and in terms of the preferred embodiments, it is to be understood that the invention is not limited to the disclosed embodiments. On the contrary, it is intended to cover various modifications and similar arrangements (as would be apparent to those skilled in the art). Therefore, the scope of the appended claims should be accorded the broadest interpretation so as to encompass all such modifications and similar arrangements.

What is claimed is:

1. A lithium transition metal composite oxide powder, comprising a plurality of biwedge octahedron particles represented by a general formula: $Li_aNi_bMn_cCo_dM_eO_f$, wherein $0.5 \leq a \leq 2$, $b+c+d+e=1$, $0<b<1$, $0<c<1$, $0 \leq d<1$, $0 \leq e<0.15$, $2 \leq f \leq 3$, and M is at least one of Mg, Sr, Ba, Cd, Zn, Al, Ga, B, Zr, Ti, Ca, Ce, Y, Nb, Cr, Fe and V.

2. The lithium transition metal composite oxide powder as claimed in claim 1, wherein the biwedge octahedron particle has a plurality of trenches on its surface.

3. The lithium transition metal composite oxide powder as claimed in claim 2, wherein the trenches are distributed throughout an entire surface of the particle.

4. The lithium transition metal composite oxide powder as claimed in claim 2, wherein the trench has a width ranging from 100 nm to 300 nm.

5. The lithium transition metal composite oxide powder as claimed in claim 1, wherein an average size of the particles ranges from 1 to 25 μm.

6. The lithium transition metal composite oxide powder as claimed in claim 1, wherein a total pore volume of the particle is between 0.001 and 0.02 $cm^3/g$.

7. The lithium transition metal composite oxide powder as claimed in claim 1, wherein the particles have a spinel-type crystal structure, a layer-layer crystal structure, or a layer crystal structure.

8. The lithium transition metal composite oxide powder as claimed in claim 1, wherein the particles have a width-to-thickness ratio ranging from 1.5 to 4.6.

9. The lithium transition metal composite oxide powder as claimed in claim 1, wherein more than 70% of the particles have a width-to-thickness ratio ranging from 1.5 to 4.6.

10. The lithium transition metal composite oxide powder as claimed in claim 1, wherein the particles are doped with sulfur or fluorine.

11. The lithium transition metal composite oxide powder as claimed in claim 1, wherein the particles are surface coated with a protective layer comprising fluorine, sulfur, metal fluoride, metal hydroxide or a combination thereof.

12. The lithium transition metal composite oxide powder as claimed in claim 11, wherein the metal oxide or metal hydroxide is $ZrO_2$, $Al_2O_3$, MgO, AlOOH, TiO, $TiO_2$, $Y_2O_3$ or $SiO_2$.

13. A lithium ion battery, comprising:
a positive electrode, and a negative electrode;
a separator disposed between the positive electrode and negative electrode;
an electrolyte disposed in the separator,
wherein the positive electrode comprises the lithium transition metal composite oxide powder of claim 1 as an active material of the positive electrode.

* * * * *